US00PP26992P3

(12) United States Plant Patent
Wood

(10) Patent No.: US PP26,992 P3
(45) Date of Patent: Aug. 2, 2016

(54) ***SPIRAEA* PLANT NAMED 'SMNSJSP'**

(50) Latin Name: *Spiraea japonica*
Varietal Denomination: SMNSJSP

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 17 days.

(21) Appl. No.: 14/544,346

(22) Filed: Dec. 23, 2014

(65) Prior Publication Data

US 2016/0183429 P1 Jun. 23, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/0216; A01H 5/00
See application file for complete search history.

*Primary Examiner* — Kent L Bell
(74) *Attorney, Agent, or Firm* — Cassandra Bright

(57) ABSTRACT

A new and distinct *Spiraea* cultivar named 'SMNSJSP' is disclosed, characterized by a compact habit and very abundant bright Red-Purple flowers. The new variety is a *Spiraea*, normally produced as an outdoor garden or container plant.

2 Drawing Sheets

Latin name of the genus and species: *Spiraea japonica*.
Variety denomination: 'SMNSJSP'.

BACKGROUND OF THE INVENTION

The new *Spiraea* cultivar is a product of a planned breeding program conducted by the inventor, Timothy D. Wood, in Grand Haven, Mich. The objective of the breeding program was to produce new *Spiraea* varieties of compact and full habit with new and better flower and leaf colors. The open pollination resulting in this new variety was made during June of 2007.

The parents are unknown varieties of *Spiraea japonica*; seed was bulk collected and actual parents not identified. In a block of 100 mature, flowering, unnamed seedlings that had been pretreated with 10 greys of radiation, seed was collected from ten plants evaluated to have the best foliage and flowers. This collected seed was grown out and seedlings selected for superior foliage, flower coverage and flower color. The new variety was identified as a potentially interesting selection in June of 2009, at a greenhouse in Grand Haven, Mich.

Asexual reproduction of the new cultivar 'SMNSJSP' by softwood cuttings was first performed during June of 2009, at commercial greenhouse in Grand Haven, Mich. Subsequent propagation has shown that the unique features of this cultivar are stable and reproduced true to type in 3 successive generations.

SUMMARY OF THE INVENTION

The cultivar 'SMNSJSP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNSJSP'

These characteristics in combination distinguish 'SMNSJSP' as a new and distinct *Spiraea* cultivar:

1. Bright Red-Purple flowers; most *Spiraea* flowers are typically lavender-pink.
2. Compact habit, makes a good container and garden plant.
3. Extremely heavy flowering.

PARENT COMPARISON

Parents are unknown.

COMMERCIAL COMPARISON

Plants of the new cultivar 'SMNSJSP' can be compared to the commercial variety *Spiraea* 'Galen', U.S. Plant Pat. No. 21,712. These varieties are similar in most horticultural characteristics; however 'SMNSJSP' differs in the following:

1. More compact habit.
2. More inflorescence per plant.

BRIEF DESCRIPTION OF THE PHOTOGRAPHS

Figure 1:
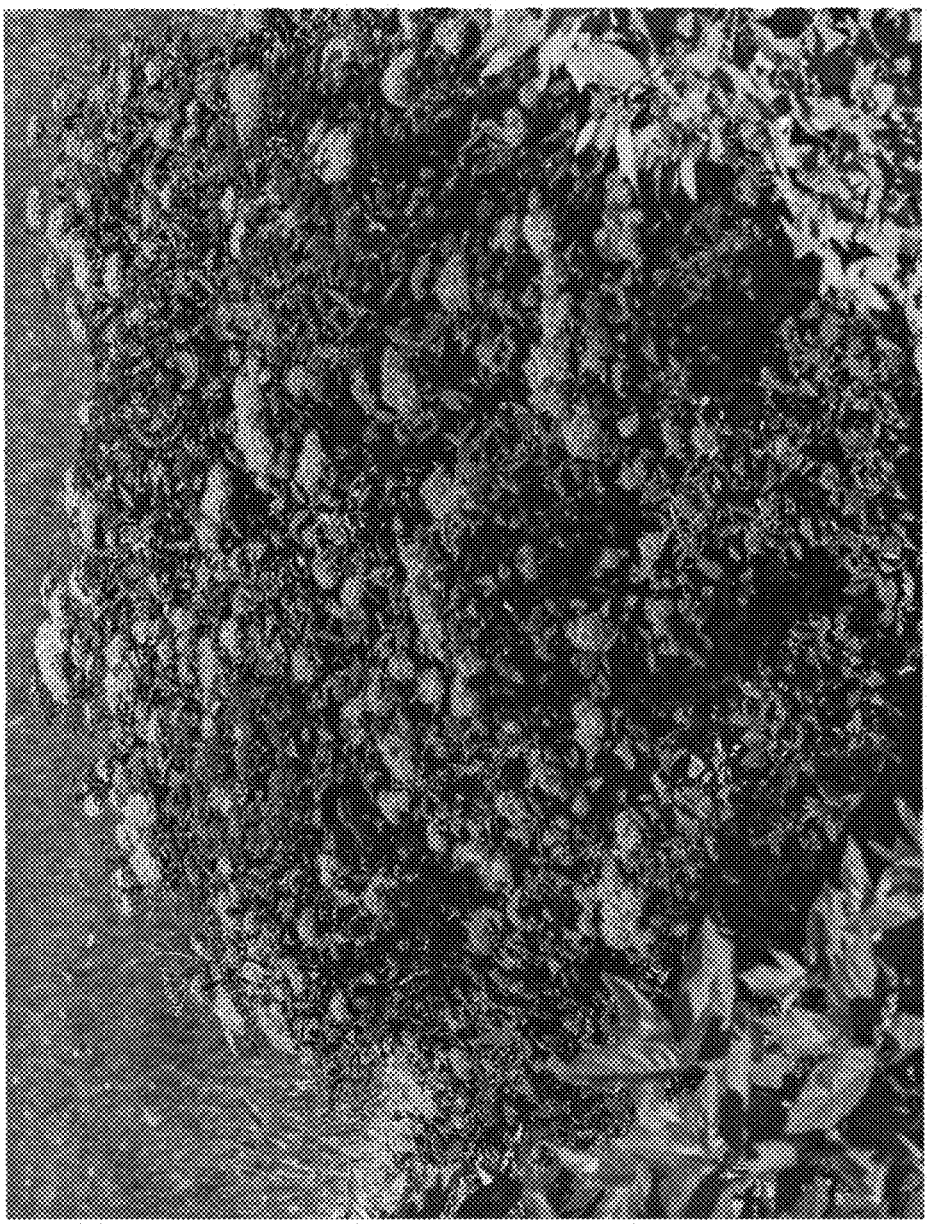

The accompanying photograph in FIG. 1 illustrates in full color a typical plant of 'SMNSJSP' grown in an outdoor flower bed, in Grand Haven, Mich.

Figure 2:
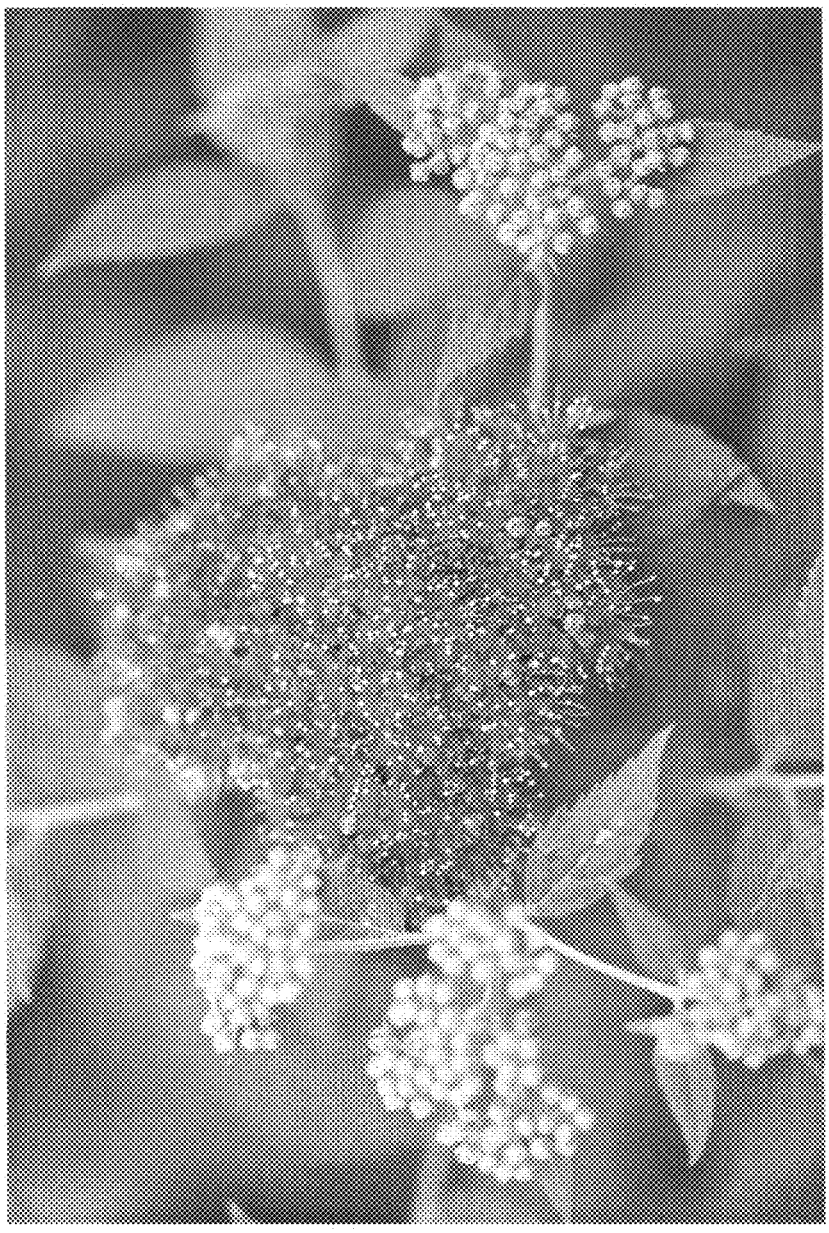

FIG. 2 illustrates in full color a typical inflorescence of 'SMNSJSP'. Age of the plant photographed is approximately 2 to 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'SMNSJSP' plants grown in a commercial nursery in Grand Haven, Mich. Measurements were taken during Mid July of 2014. The plants were 2 to 3 years old in 2 gallon containers. The growing temperature ranged from −31° C. to 38° C. The greenhouse is double poly covered though the winter. Measurements and numerical values represent averages of typical plant types.

Botanical classification: *Spiraea japonica* 'SMNSJSP'.

PROPAGATION

Time to initiate roots: About 15 days at approximately 22° C.

Root description: Fibrous, moderate to dense density medium thickness and freely branching. Cream to brown in color, not effectively measured with a color chart.

Time to produce a rooted young plant: About 2 months at 22° C.

PLANT

Plant type: Perennial shrub.

Age of plant described: Approximately 2 to 3 years old.

Growth habit: Mounded with good branching.

Pot size of plant described: 2 gallon pot.

Overall plant shape: Upright and rounded.

Height: Approximately 50 cm to top of foliage.

Plant spread: Approximately 92 cm.

Growth rate: Fast and vigorous.

Plant vigor: Strong.

Branching characteristics: Strong branching, some basal branching, some pinching required.

Length of primary lateral branches: Approximately 30.5 cm mature growth.

Diameter of lateral branches: Approximately 1.5 cm new growth, 3.0 cm for mature growth.

Quantity of lateral branches: About 26 lateral branches per main branch.

Stem:

- *Stem appearance*.—Rounded, woody, frutescent.
- *Stem strength*.—Sturdy.
- *Stem color*.—New: Near RHS Yellow-green 144B. Old: Near RHS Brown 200A.
- *Pubescence*.—None.
- *Aspect*.—Straight, at an outward angle of 45°.
- *Other plant characteristics*.—New growth branches form at internodes.

Internode length: Average 2.5 cm.

FOLIAGE

Leaf:

- *Arrangement*.—Alternate, single.
- *Leaf shape*.—Ovate.
- *Quantity*.—Approximately 12 fully expanded per main branch.
- *Average length*.—Approximately 1.8 cm. young; 5 cm. mature.
- *Average width*.—Approximately 2.5 cm.
- *Apex*.—Acute.
- *Base*.—Cuneate.
- *Margin*.—Double serrate.
- *Texture of top surface*.—Smooth, glabrous.
- *Texture of bottom surface*.—Smooth, with distinct leaf veins.
- *Color*.—Young foliage upper side: Near RHS Green 137A with a hint of Yellow-green 144A. Young foliage under side: Near RHS Green 138A with Yellow-green 150D venation. Mature foliage upper side: Near RHS Green 137A with a hint of Yellow-green 144A. Mature foliage under side: Near RHS Green 138A with Yellow-green 150D venation.
- *Venation*.—Pattern: Palmate. Color upper side: Near RHS Yellow-green 150C. Color under side: Near RHS Yellow-green 150D. Outer Branching: Near RHS Yellow-green 150C.
- *Petiole*.—Average Length: Approximately 1 cm young; 1.5 cm mature. Diameter: 1 mm. Petiole color upper side: New growth: Near RHS Yellow-green 147C. Petiole color lower side: New growth: Near RHS Yellow-green 147C. Petiole Texture upper side: Smooth. Petiole Texture lower side: Smooth.
- *Other foliage characteristics*.—Stipules at internodes, 2 mm, near RHS Red-Purple 60A.

FLOWER

Natural flowering season: Continuous flowering from late Spring through the Summer.

Inflorescence type and habit: Terminal corymb.

Flower arrangement: Single whorl rotate flowers.

Flower longevity on plant: 3-4 weeks.

Quantity of flowers per inflorescence: Average 300 to 400.

Inflorescence size:

- *Width*.—Approximately 4.5 cm.
- *Height*.—Approximately 2 cm young; 3 cm mature.

Quantity of inflorescence per lateral stem: 16.

Quantity of inflorescence per plant: 200 to 700.

Individual flowers:

- *Flower form*.—Rotate.
- *Flower aspect*.—Upright and outward.
- *Flowering habit*.—Blooms freely on terminal corymbs.
- *Size*.—Diameter: Approximately 6 mm. Length: Approximately 6 mm. Depth: Approximately 6 mm.

Flower other characteristics:

- *Persistence*.—Self cleaning.
- *Fragrance*.—None.

Petal:

- *Petal arrangement*.—Single whorl of five petals.
- *Number of petals per flower*.—5.
- *Petal shape*.—Globose.
- *Petal base*.—Obtuse.
- *Margin*.—Entire.
- *Tip shape*.—Widely obtuse.
- *Length*.—3 mm.
- *Width*.—2.5 mm.
- *Texture*.—Upper: Smooth, Glabrous. Lower: Smooth, Glabrous.

Petal color:

- *When opening*.—Upper surface: Near RHS Red-purple 70A. Lower surface: Near RHS Red-purple 70C.
- *Fully opened*.—Upper surface: Near RHS Violet 83B. Lower surface: Inner stippling near RHS Red-Purple 58B surrounded by RHS Violet 87C, shading to Violet 83A.

Bud:

*Shape*.—Globose.

*Length*.—Approximately 3 mm.

*Diameter*.—Approximately 3 mm.

*Color*.—Base of bud near RHS Yellow-green 145C shading to Red-purple 70A.

Sepals:

*Shape*.—Acute.

*Arrangement*.—Single whorl of 5 sepals.

*Number of sepals*.—5.

*Length*.—Approximately 1 mm.

*Width*.—Approximately 1 mm.

*Margin*.—Entire.

*Base*.—Fused.

*Tip*.—Acute.

*Texture*.—Smooth.

*Color*.—Upper side: Near RHS Red-Purple 59A. Lower side: Near RHS Red-Purple 70C.

Peduncle:

*Length*.—24 mm.

*Diameter*.—15 mm.

*Color*.—Near RHS Yellow-Green 144A.

*Orientation*.—Upright and outward.

*Strength*.—Strong.

*Texture*.—Smooth, glabrous.

Pedicel:

*Length*.—5 mm.

*Diameter*.—0.8 mm.

*Color*.—Near RHS Yellow-Green 145A.

*Orientation*.—Upright and outward.

*Strength*.—Strong.

*Texture*.—Smooth.

REPRODUCTIVE ORGANS

Stamens:

*Number*.—Approximately 26.

*Filament length*.—3 mm.

*Filament color*.—Near RHS Red-Purple 70B.

Anthers:

*Shape*.—Globose.

*Length*.—Approximately 0.25 mm.

*Color*.—Near RHS Black 202A.

*Pollen color*.—RHS White 155B.

Pistil:

*Number*.—5.

*Length*.—Approximately 2 mm.

*Style*.—Length: Approximately 1 mm. Color: Near RHS Red-purple 70B.

*Stigma*.—Shape: Globose. Color: Near RHS Red-Purple 70B. Ovary color: Near RHS Yellow-Green 144C.

OTHER CHARACTERISTICS

Seeds and fruits: Not observed to date.

Garden performance: Excellent performance in a garden setting.

Disease/pest resistance: Good mildew resistance observed. Neither resistance nor susceptibility to normal diseases and pests of *Spiraea* have been observed.

Temperature tolerance: The new variety tolerates temperatures between −31° C. to 38° C.

What is claimed is:

1. A new and distinct cultivar of *Spiraea* plant named 'SMNSJSP' as herein illustrated and described.

* * * * *